United States Patent
Blomqvist et al.

(10) Patent No.: US 8,812,109 B2
(45) Date of Patent: Aug. 19, 2014

(54) METHOD AND SYSTEM FOR STIMULATING A HEART OF A PATIENT

(75) Inventors: Andreas Blomqvist, Taby (SE); Kjell Noren, Solna (SE)

(73) Assignee: St. Jude Medical AB, Jarfalla (SE)

( * ) Notice: Subject to any disclaimer, the term of this patent is extended or adjusted under 35 U.S.C. 154(b) by 7 days.

(21) Appl. No.: 13/593,334

(22) Filed: Aug. 23, 2012

(65) Prior Publication Data

US 2013/0158620 A1 Jun. 20, 2013

(30) Foreign Application Priority Data

May 31, 2011 (EP) ..................................... 11168288

(51) Int. Cl.
*A61N 1/00* (2006.01)

(52) U.S. Cl.
CPC ........................................ *A61N 1/00* (2013.01)
USPC ........................................................... 607/23

(58) Field of Classification Search
CPC ............ A61N 1/00; A61N 1/02; A61N 1/04; A61N 1/05; A61N 1/08; A61N 1/10–1/16; A61N 1/18; A61N 1/20; A61N 1/025; A61N 1/32; A61N 1/39; A61N 1/40; A61N 1/362; A61N 1/372; A61N 1/0404; A61N 1/36014
See application file for complete search history.

(56) References Cited

U.S. PATENT DOCUMENTS

| | | | |
|---|---|---|---|
| 7,149,587 B2 | 12/2006 | Wardle et al. | |
| 7,483,743 B2 | 1/2009 | Mann et al. | |
| 7,515,971 B1 | 4/2009 | Doan | |
| 2006/0224204 A1 | 10/2006 | Hettrick et al. | |
| 2009/0299429 A1* | 12/2009 | Mayotte | ........................ 607/18 |
| 2010/0234906 A1 | 9/2010 | Koh | |

* cited by examiner

*Primary Examiner* — Christopher D Koharski
*Assistant Examiner* — Elizabeth K So

(57) ABSTRACT

In an implantable medical device and a method for stimulating a heart of a patient, at least one left atrial pressure (LAP) signal over a cardiac cycle is obtained. The A-wave is identified using the LAP signal and a maximum positive rate of change of the A-wave of the LAP signal is determined. The maximum positive rate of change of the A-wave corresponds to the rate which the pressure in the atrium raises as the atria contraction forces more blood into the ventricle during the very last stage of diastole. Further, AV and/or VV delay is adjusted in response to the maximum positive rate of change of the A-wave, wherein a reduction of the maximum positive rate of change of the A-wave indicates an AV and/or VV delay providing an enhanced hemodynamic performance.

13 Claims, 7 Drawing Sheets

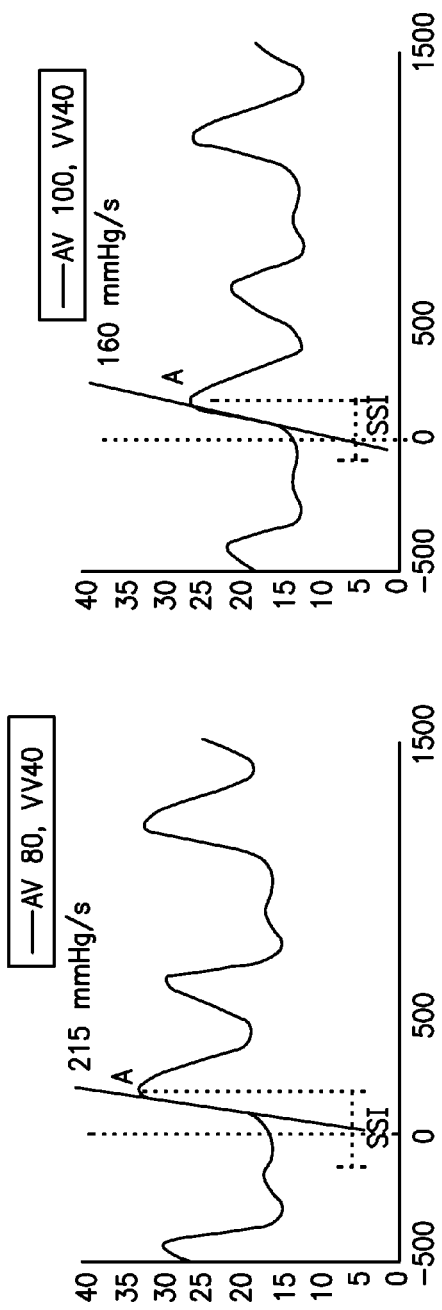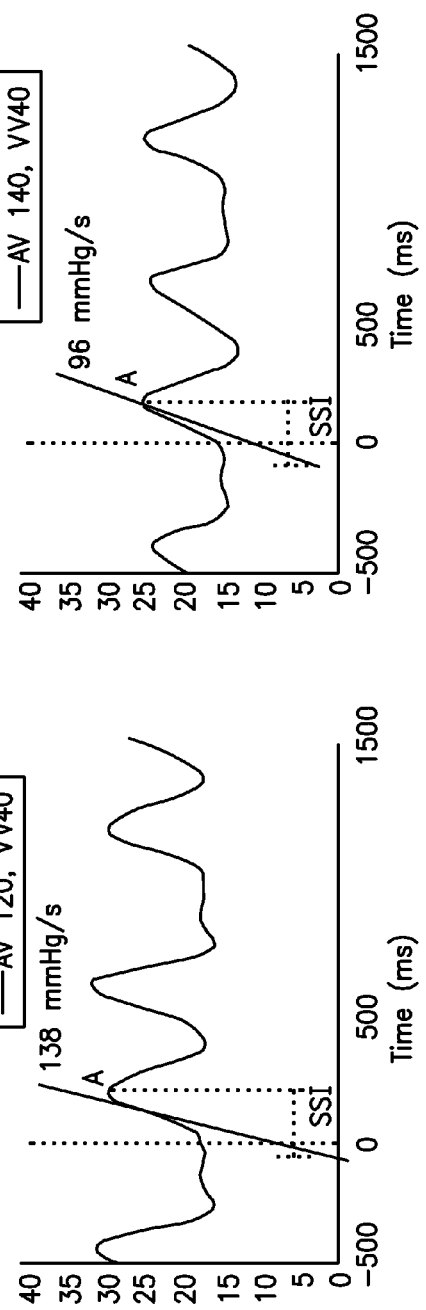
FIG. 3a  FIG. 3b
FIG. 3c  FIG. 3d

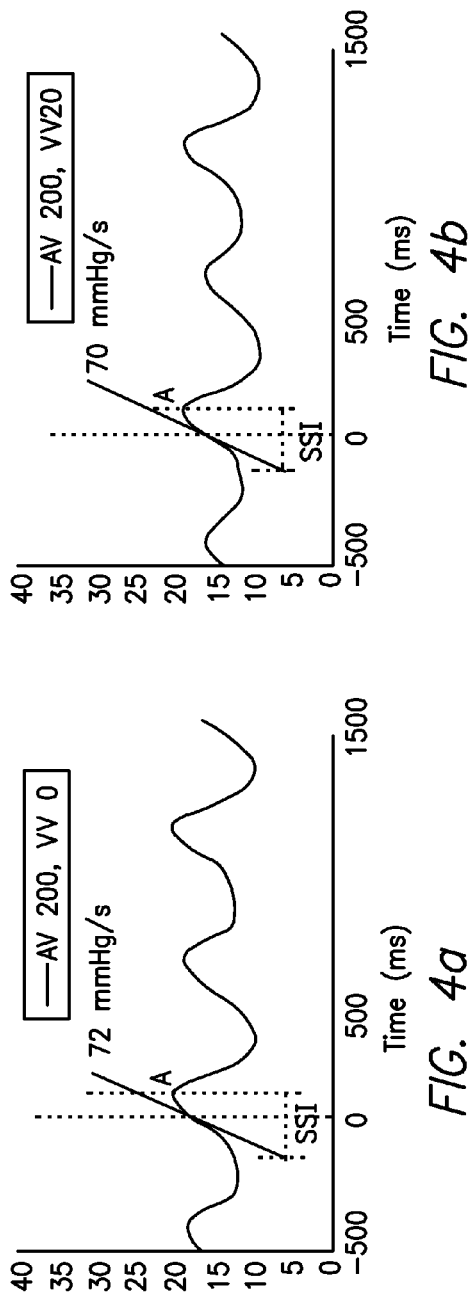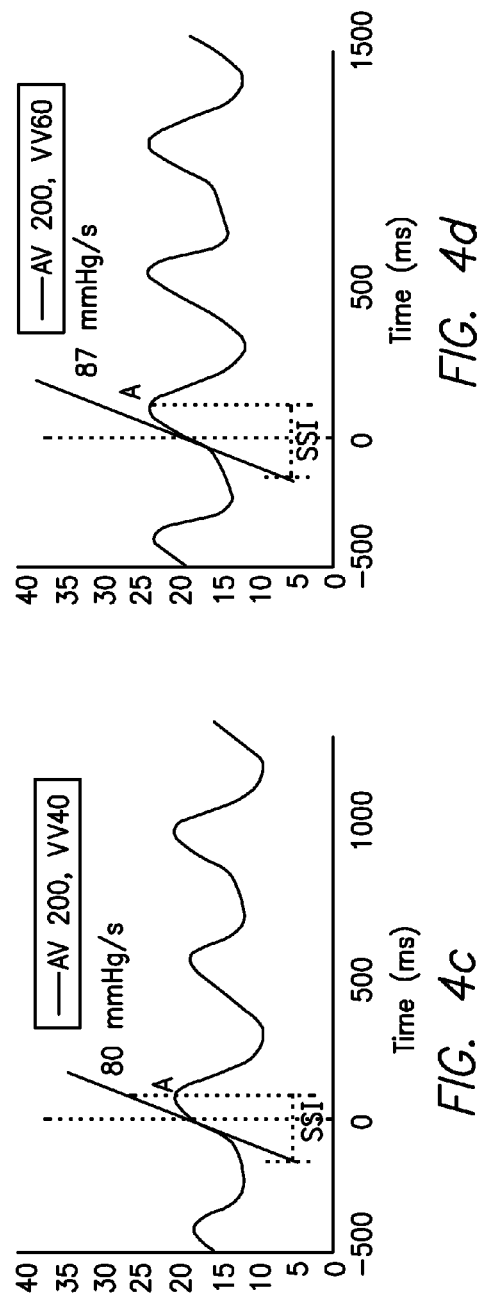
FIG. 4a
FIG. 4b
FIG. 4c
FIG. 4d

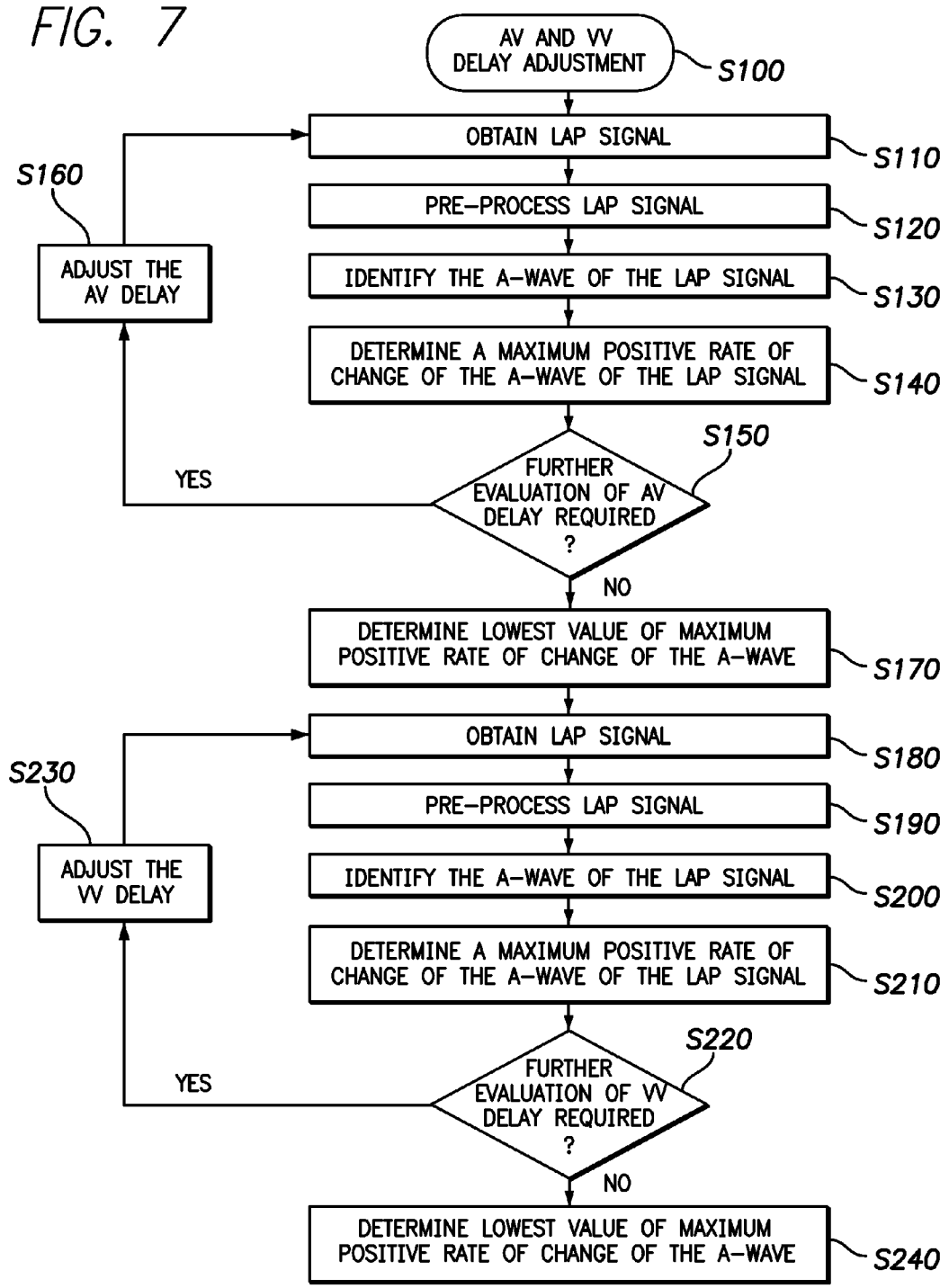

METHOD AND SYSTEM FOR STIMULATING A HEART OF A PATIENT

FIELD OF THE INVENTION

The present invention relates generally to implantable medical devices and more particularly to systems and methods for stimulating a heart of a patient.

BACKGROUND OF THE INVENTION

Heart failure is usually a chronic, long term condition, but may occur suddenly. It may affect the left heart, the right heart, or both sides of the heart. Heart failure may be considered as a cumulative consequence of all injuries and/or stress to the heart over a person's life and the prevalence of heart failure increases constantly. For example, it is estimated that nearly 5 million people in the USA suffer from heart failure and about 400.000 new cases are diagnosed every year. The prevalence of heart failure approximately doubles with each decade of life. Thus, HF has a huge impact on both health economy and the well-being of the people in western society.

Cardiac resynchronization therapy (CRT) is an established method to treat HF in patients with low ejection fraction and widened QRS-complex. The optimal method to monitor the effects of CRT is however under debate. Several sensor techniques have been developed for providing input cardiac data for use in optimizing CRT but so far the medical community has not fully accepted any of the proposed techniques. Most attempts of proving the clinical benefits of CRT optimization have failed. There are some results supporting AVD-optimization (atrioventricular delay) but in fact really no study has shown significant impact of VV-optimization (inter-ventricular delay). There are many conceivable reasons for the lack of results, as briefly touched upon earlier, one reason might be that none of the sensors available can fully replace the qualified judgment of a skilled physician with both sensor output and routine as tools in evaluating a patient's response to CRT—since many of the presented concepts focus solely on the systole. However, there is reason to believe that a more holistic view on the hemodynamics is required to provide reliable optimization of the CRT both for current responders and potentially also for patients that are so called non-responders.

Left atrial pressure (LAP) is a signal that divulges interesting information about the hemodynamics of the patient. In fact, the LAP signal, or the mean of the LAP signal is by many regarded as a reliable measure for use in diagnosis of congestive heart failure and is also successfully used to e.g. titrate drugs (such as diuretics) for heart failure (HF) patients. Clearly, the primary focus and use of LAP has been the study and use of LAP mean, i.e. the average value of the LAP signal over a number of heart cycles.

In U.S. Published Application No. 2006/0224204, methods and systems for adjusting parameters of an implantable medical device in response to a left atrial pressure signal is shown. The LAP signals are analyzed to identify certain characteristics, attributes and/or signal morphologies that correlate to cardiac performance of the patient, which in turn can be used for the adjustment of the operating parameters. Timing relationships of LAP signal attributes and in particular various timing intervals between the v-wave, a-wave and c-wave characteristics can be used for AV delay adjustment. Specifically, the slope of the LAP signal between the a-wave peak and the c-wave peak, the slope of the LAP signal between the c-wave peak and the x-wave valley, and/or the slope of the LAP signal between the x-wave valley and the v-wave peak can be used for optimizing AV delay and other device parameters. The slope of a specific segment of the LAP signal can be maximized in order to optimize the AV delay.

However, there is a need within the art for improved and alternative methods and system that utilized the valuable information content of the LAP signal for optimizing CRT settings such as AV and/or VV delays.

SUMMARY OF THE INVENTION

An object of the present invention is to provide a system, a cardiac stimulator and a method for further improvements in optimization of AV and VV delays for use in, for example, CRT.

A further object of the present invention is to provide improved and alternative cardiac stimulators, systems and methods for utilizing the information content of the LAP signal for optimizing CRT settings such as AV and/or VV delays.

According to an aspect of the present invention there is provided a method for adjusting AV and VV delay of a cardiac stimulator. The method comprises obtaining at least one left atrial pressure, LAP, signal over a cardiac cycle. The A-wave is identified using the LAP signal and a maximum positive rate of change of the A-wave of the LAP signal is determined. The maximum positive rate of change of the A-wave corresponds to the rate which the pressure in the atrium raises as the atrial contraction forces more blood into the ventricles during the very last stage of diastole. Further, AV and/or VV delay is adjusted in response to the maximum positive rate of change of the A-wave, wherein a reduction of the maximum positive rate of change of the A-wave indicates an AV and/or VV delay providing an enhanced hemodynamic performance.

According to a second aspect of the present invention, there is provided a cardiac stimulator comprising a data collection module configured to obtain at least one left atrial pressure, LAP, signal reflecting cardiac behavior over a cardiac cycle from a left atrial pressure sensor connectable to said cardiac stimulator. Further, the cardiac stimulator comprises a LAP signal processing module coupled to said data collection module and being configured to identify the A-wave using the LAP signal and to determine a maximum positive rate of change of the A-wave of the LAP signal. A parameter setting adjusting module coupled to the LAP signal processing module is configured to adjust AV and/or VV delay of said cardiac stimulator in response to the maximum positive rate of change of the A-wave, wherein a reduction of the maximum positive rate of change of the A-wave indicates an enhanced hemodynamic performance.

Thus, the present invention is based on the insights that the information content of the LAP signal can be more efficiently utilized for extracting relevant physiological information that, in turn, can be used for optimizing CRT intervals. Specifically, the inventors have found that LAP signal contains morphological information that can be extracted to design a control parameter for optimizing AV and VV delays. In that regard, the positive rate of change of the A-wave has been found to constitute a reliable, accurate and repeatable measure of the cardiac behavior and a reduced positive rate of change of the A-wave have been verified to correlate to an improved cardiac function. Therefore, by minimizing the maximum positive rate of change of the A-wave, an optimal AV and/or VV delay can be determined. Studies performed by the inventors show that this measure provides a sensitive parameter for AV and/or VV delay settings that can be minimized for optimizing the delay setting. Further, it has also been shown that the optimization can be performed in a consistent manner for in principle all patients.

According to embodiments of the present invention, the AV and/or VV delay is optimized in response to the maximum positive rate of change of the A-wave, wherein a minimum of the maximum positive rate of change of the A-wave or a value of the maximum positive rate of change of the A-wave being below a predetermined threshold indicates an AV and/or VV delay providing an optimal hemodynamic performance.

According to embodiments of the present invention, the derivative of the LAP signal is calculated and a maximum positive rate of change of the A-wave of the LAP signal is determined by identifying the maximum value of the derivative of the LAP signal within a predetermined search window.

According to embodiments of the present invention, the predetermined search window starts at the P-wave and has a duration between 200-280 ms, and preferably between 220-260 ms, and more preferably of about 250 ms.

According to embodiments of the present invention, the time point of the mitral valve closure, MC, in the LAP signal and/or in the derivative of the LAP signal, is identified. The predetermined search window is then set to start between 200-280 ms, and preferably between 220-260 ms, and more preferably of about 250 ms, before the time point of MC and set to end at MC.

According to embodiments of the present invention, the predetermined search window has a length of the AV delay of said cardiac stimulator and starts at the P-wave.

According to embodiments of the present invention, the AV and/or VV delay is optimized in response to the maximum positive rate of change of the A-wave, wherein a minimum of the maximum positive rate of change of the A-wave or a value of the maximum positive rate of change of the A-wave being below a predetermined threshold indicates an AV and/or VV delay providing an optimal hemodynamic performance. A threshold may be used to quickly obtain an adjusted AV and VV delay. For example, it may be determined that an optimal AV delay has been achieved when the maximum positive rate of change of the A-wave for the first AV delay and VV delay in a set or protocol of AV delays is below the threshold. Thus, in such a case it is only necessary to evaluate AV delays until the first AV delay providing a value of the maximum positive rate of change of the A-wave being below the threshold is found. The same procedure may also be performed to find an optimal VV delay. However, in a case where no AV delay can be found that provides a maximum positive rate of change of the A-wave below the threshold, the threshold can be adjusted to be higher or an adjusted VV delay can be used as fixed VV delay. The threshold is patient specific and drug specific and will hence have to be determined for each individual patient and the threshold may have to be adjusted if, for example, a new drug regime is implemented for the patient. The threshold may be determined on empirical data for a specific patient.

There are further procedures for finding the lowest maximum positive rate of change of the A-wave for the AV and VV delay, for example, by performing a full grid search (i.e. evaluating each combination of AV and VV delays in a matrix of AV and VV delays) or by first finding an optimal AV delay using a fixed VV delay and thereafter optimizing the VV delay using the optimal AV delay as fixed AV delay.

Hence, in embodiments of the present invention, the step of adjusting the AV and/or VV delay comprises: selecting a matrix of AV and VV delays, determining the maximum positive rate of change of the A-wave for combinations of AV and VV delays in said matrix, and determining a combination of AV and VV delays corresponding to a minimum of the maximum positive rate of change of the A-wave or corresponding to a value of the maximum positive rate of change of the A-wave below a predetermined threshold to be an optimal AV and VV delay.

Furthermore, according to an embodiment of the present invention, the step of adjusting the AV and/or VV delay includes: (i) selecting a set of AV delays and a fixed VV delay; (ii) determining the maximum positive rate of change of the A-wave for combinations of AV delays and the fixed VV delay; (iii) identifying the AV delay providing the minimum of the maximum positive rate of change of the A-wave or corresponding to a value of the maximum positive rate of change of the A-wave below a predetermined threshold; (iv) selecting a set of VV delays and said AV delay providing the minimum of the maximum positive rate of change of the A-wave or corresponding to a value of the maximum positive rate of change of the A-wave below a predetermined threshold; (v) determining the maximum positive rate of change of the A-wave for combinations of VV delays and the fixed AV delay; (vi) identifying the VV delay providing the minimum of the maximum positive rate of change of the A-wave or corresponding to a value of the maximum positive rate of change of the A-wave below a predetermined threshold; and (vii) determining the AV delay and the VV delay corresponding to a minimum of the maximum positive rate of change of the A-wave or corresponding to a value of the maximum positive rate of change of the A-wave below a predetermined threshold to be optimal AV and VV delays. A start delay for the VV delay can be found, for example, by using a prior art optimization procedure such as QuickOpt™ provided by the applicant.

It is however not necessary to start the adjustment process by finding the optimal AV delay but is alternatively possible to first find the optimal VV delay and thereafter use the optimal VV delay and evaluate different AV delays.

The results provided by the present invention, i.e. a set of AV and VV delay providing the minimum value of the maximum positive rate of change of the A-wave may also be used by the physician as input values when determining the therapy for a patient, for example, in connection with other technological means, such as echocardiography, and prior experience.

Further objects and advantages of the present invention will be discussed below by means of exemplifying embodiments.

These and other features, aspects and advantages of the invention will be more fully understood when considered with respect to the following detailed description, appended claims and accompanying drawings.

BRIEF DESCRIPTION OF THE DRAWINGS

Exemplifying embodiments of the invention are illustrated by way of example and not by way of limitation in the figures of the accompanying drawings in which like references indicate similar elements. It should be noted that references to "an" or "one" embodiment in this discussion are not necessarily to the same embodiment, and such references mean at least one.

FIGS. 3a-3h are diagrams showing the LAP signal over time for a number of different combinations of AV delays and a fixed VV delay. The maximum positive rate of change of the A-wave is also shown for respective combination of AV and VV delay;

FIGS. 4a-4d are diagrams showing the LAP signal over time for a number of different combinations of VV delays and a fixed AV delay. The maximum positive rate of change of the A-wave is also shown for respective combination of AV and VV delay;

FIG. 7 is a flow diagram of an AV and VV delay adjustment process, which may be performed by a cardiac stimulator configured in accordance with example embodiments of the invention.

DESCRIPTION OF THE PREFERRED EMBODIMENTS

The following is a description of exemplifying embodiments in accordance with the present invention. This description is not to be taken in limiting sense, but is made merely for the purposes of describing the general principles of the invention. It is to be understood that other embodiments may be utilized and structural and logical changes may be made without departing from the scope of the present invention. Some embodiments of the present invention relate generally to implantable pressure sensors but, however, even though particular types of pressure sensors are mentioned herein, the present invention is not limited to pressure sensors but may include other types of hemodynamic sensors such as, accelerometers, blood flow probe, load indicators which react to geometrical changes, heart sound sensors, or photoplethysmography sensors or similar sensors.

Figure 1:
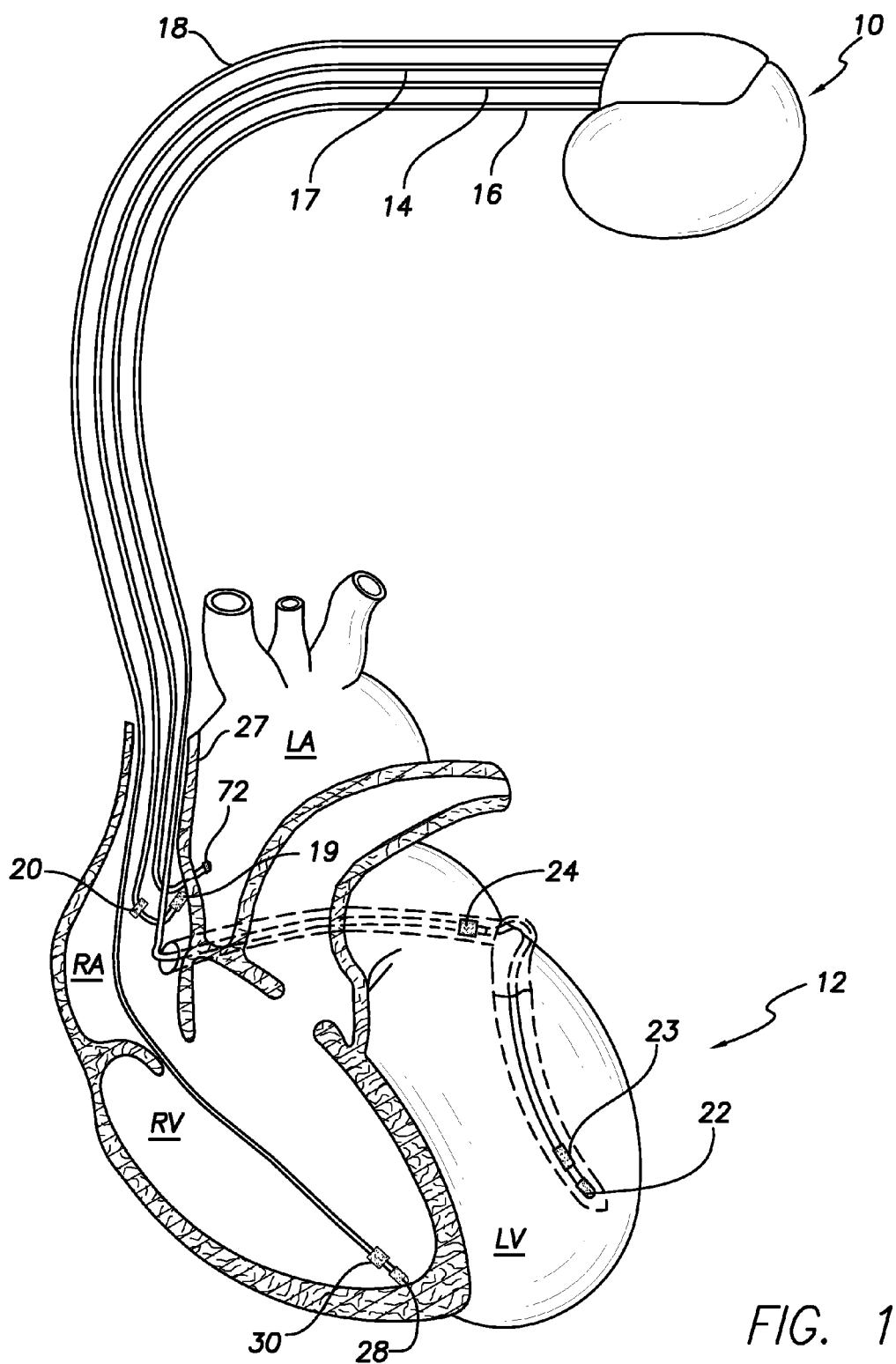
FIG. 1 is a simplified and schematic diagram of one embodiment of a system configuration according to the present invention including an implantable stimulation device in electrical communication with several leads implanted in a patient's heart for detecting cardiac activity and for delivering multi-chamber stimulation.

Referring first to FIG. 1, one implementation of the present invention relating to a system including an implantable cardiac stimulator connectable to one or more medical leads will be discussed.

The implantable cardiac stimulator 10 is in electrical communication with a patient's heart 12 by way of four leads 14, 16, 17 and 18 suitable for delivering multi-chamber stimulation therapy.

The cardiac stimulator 10 is connectable to a right atrium lead 14 comprising a LAP sensor 72 that provides real-time LAP signals to the cardiac stimulator 10 from the left atrium of the heart 12. The LAP sensor 72 is implanted into left atrium through the septal wall 27 of the heart 12. Embodiments of such LAP sensors that may be used in the present invention are disclosed in U.S. Pat. No. 7,515,971 to Doan or in WO 2005/107583 to Eigler et al, which hereby are incorporated herein by reference.

To sense atrial signals and to provide right atrial chamber stimulation therapy, the stimulator 10 is coupled to an implantable right atrial lead 17 having, for example, an atrial tip electrode 19, which typically is implanted in the patient's right atrial appendage or septum. FIG. 1 shows the right atrial lead 17 as also having an atrial ring electrode 20.

The cardiac stimulator 10 is in electrical communication with the heart 12 by way of an implantable right ventricular lead 18 having, in this embodiment, a right ventricular tip electrode 28 and a right ventricular ring electrode 30. Typically, the right ventricular lead 18 is transvenously inserted into the heart 12 to place the right ventricular tip electrode 28 in the right ventricular apex. The right ventricular lead 18 is capable of sensing or receiving cardiac signals, and delivering stimulation in the form of pacing therapy.

The cardiac stimulator 10 may further sense left atrial and ventricular cardiac signals and provide left chamber pacing therapy via the coronary sinus lead 16 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible via the coronary sinus.

The coronary sinus lead 16 is designed to receive atrial and ventricular pacing signals and to deliver left ventricular pacing therapy using, for example, a left ventricular tip electrode 22 and a left ventricular ring electrode 23, and deliver left atrial pacing therapy using a left atrial ring electrode 24.

In operation, the cardiac stimulator 10 obtains data about the heart 12 via the leads 14, 16, 17 and 18 and possibly via other data providing units. This data is provided to the internal processor 41 (see FIG. 2), which analyses the data and provides a response as appropriate. In particular, the cardiac stimulator 10 generates one or more therapy signals that are preferably optimized in accordance with the obtained data. In example embodiments, the cardiac stimulator 10 selects or adjusts an electrical stimulation therapy based on obtained left atrial pressure data as will be described below.

Figure 2:
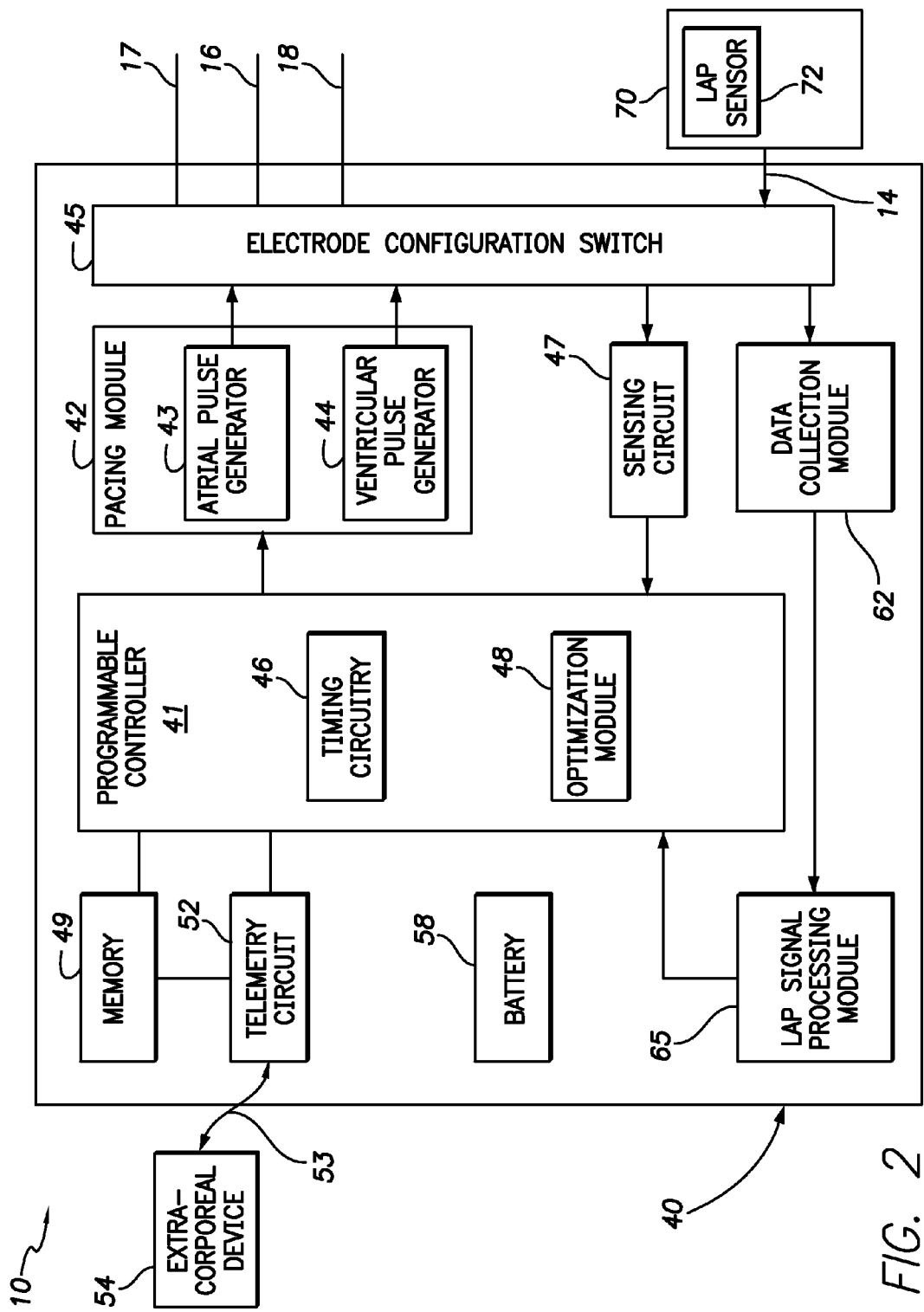
FIG. 2 is a simplified functional block diagram of one embodiment of a system in accordance with the present invention, illustrating basic elements of the system.

In FIG. 2, an exemplary, simplified block diagram depicting various components of the cardiac stimulator according to embodiments of the present invention is shown. The cardiac stimulator 10 is capable of delivering cardiac resynchronization therapy and is configured to integrate both monitoring and therapy features, as will be described below. The cardiac stimulator 10 collects and processes data about the heart 12 from one or more sensors including at least one left atrial pressure sensor 72. Further, the cardiac stimulator 10 collects and processes data about the heart 12 from electrode pairs for sensing cardiac electrogram (EGM) signals. While a particular multi-chamber device is shown, it is to be appreciated and understood that this is done for illustration purposes only. Thus, the techniques and methods described below can be implemented in connection with any suitable configured or configurable stimulation device. Accordingly, one of skill in the art could readily duplicate, eliminate, or disable the appropriate circuitry in any desired combination to provide a device capable of treating the appropriate chamber with pacing stimulation including cardiac resynchronization therapy.

The cardiac stimulator 10 has a housing 40, often referred to as the "can" or "case electrode". The housing 40 may function as a return electrode in "unipolar" modes. Further, the housing 40 includes connector (not shown) having a plurality of terminals (not shown) for connection with electrodes and/or sensors.

The cardiac stimulator 10 includes a programmable microcontroller or control module 41 that inter alia controls the various modes of stimulation therapy. As well known within the art, the microcontroller 41 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 41 includes the ability to process or monitor input signals (data or information) as controlled by a program stored in a designated block of memory. The type of microcontroller is not critical to the described implementations. Rather, any suitable microcontroller 41 may be used that carries out the functions described herein. The use of micro-processor based control circuits for performing timing and data analysis are well known in the art.

Furthermore, the cardiac stimulator 10 includes pacing module 42 adapted to provide pacing signals for delivery to the patient. The pacing module 42 comprises an atrial pulse generator 43 and a ventricular pulse generator 44 that generate pacing stimulation pulses for delivery by the right atrial lead 17, the coronary sinus lead 16, and/or the right ventricular lead 18 via an electrode configuration switch 45. It is understood that in order to provide stimulation therapy in each of the four chambers, the atrial and ventricular pulse generators 43 and 44, may include dedicated, independent pulse generators, multiplexed pulse generators, or shared pulse generators. The pulse generators 43 and 44 are controlled by the microcontroller 41 via appropriate control signals to trigger or inhibit stimulation pulses.

The microcontroller 41 further includes timing control circuitry 46 to control timing of the stimulation pulses (e.g. pacing rate, AV delay, VV delay, etc.) as well as to keep track of timing of refractory periods, blanking intervals, etc. which is well known in the art. In addition, the microcontroller 41 may include components such as e.g. an arrhythmia detector (not shown) and/or a morphology detector (not shown).

The LAP sensor 72 is configured to measure real-time LAP of the patient's heart and to provide raw LAP data to a data collection module 62. The obtained LAP data may be processed in the data collection module 62 and/or in a LAP data processing module 65 so as to convert the raw LAP data signal into a digital LAP signal and/or a digital signal including the derivative of the LAP signal for use in further analysis. Suitable LAP sensors include, but are not limited to, LAP sensors that are mounted through the atrial septal wall of the heart.

A sensing circuit 47 that includes atrial sensing circuits and ventricular sensing circuits may also be coupled to the right atrial lead 17, the coronary sinus lead 16, and the right ventricular lead 18 (see FIG. 1) through the switch 45 for detecting the presence of cardiac activity in each of the four chambers of the heart. Accordingly, the atrial sensing circuits and ventricular sensing circuits 47 may include dedicated sense amplifiers, multiplexed amplifiers, or shared amplifiers.

The output from the atrial sensing circuits and ventricular sensing circuits 47 are coupled to the microcontroller 41, which, in turn, is able to trigger or inhibit the atrial sensing circuits and ventricular sensing circuits 47 in a demand fashion in response to the absence or presence of cardiac activity in the appropriate chamber of the heart.

Furthermore, the microcontroller 41 is coupled to a memory 49 by a suitable data/address bus (not shown), wherein the programmable operating parameters used by the microcontroller 41 are stored and modified, as required, in order to customize the operation of the cardiac stimulator to the needs of a particular patient. Such operating parameters define, for example, pacing pulse amplitude, pulse duration, etc. Advantageously, the operating parameters may be non-invasively programmed into the memory 49 through a communication module 52 including, for example, a telemetry circuit for telemetric communication via communication link 53 with an external device 54, such as a programmer or a diagnostic system analyzer. The telemetry circuit advantageously allows intracardiac electrograms and status information relating to the operation of the device 10 to be sent to the external device 54 through an established communication link 53. Further, the communication module may alternatively or as a complement to the telemetry circuit include circuit for RF communication.

Moreover, the cardiac stimulator 10 additionally includes a battery 58 that provides operating power to all of the circuits shown in FIG. 2. Preferably, the stimulator 10 employs lithium or similar battery technology.

The data collection module 62 suitably interacts with one or more data providing units to obtain data about the patient. The data providing units includes, for example, sources of information about the patient's heart. In embodiments of the present invention, the data providing unit comprises an ECG unit (not shown) that provides electrical impulses or other observed signals that can be used to model the patient's ECG waveform. One data providing unit 70 includes the LAP sensor 72 for providing LAP signals and may, in addition, include an accelerometer or a heart rate sensor.

The data collection module 62 is configured to obtain data about the patient including LAP signals from the LAP sensor 72, for example, during different AV delays and VV delays for later processing of the data. The data collection module 62 comprises, for example, analog-to-digital (ND) data acquisition circuits adapted to acquire and amplify the signals from the LAP sensor 72 and to convert the raw analog data into a digital signal, filter the signals and store the digital signals for later processing in a LAP signal processing module 65, which also may be integrated in the microcontroller 41.

According to embodiments of the present invention, the LAP signal processing module 65 is configured to identify the A-wave using the LAP signal and determine a maximum positive rate of change of the A-wave of the LAP signal. The positive presystolic A-wave is produced by the right atrial contraction and the peak of the A-wave coincides with the closure of the Mitral Valve (MC).

The LAP signal processing module 65 may include filter circuits configured to, for example, perform a smoothing process and/or high pass filtering (e.g. to remove respiration artifacts) and/or low pass filtering. In one embodiment of the present invention, the LAP signal is band-pass filtered, for example, with a filter having a band-pass range of 0.75 Hz to 30 Hz, to remove both high frequency noise and respiration artifacts.

Further, the LAP signal processing module 65 is configured to perform a gradient calculation. Based on the LAP gradient, a cardiac event search can be performed to identify certain cardiac events, such as, for example, time point of Mitral valve closure (MC) and Mitral valve opening (MO). The peak of the A-wave coincides with MC and the peak of the V-wave coincides with MO.

In embodiments of the present invention, a search interval may be set to have a duration between 200-280 ms, and preferably between 220-260 ms, and more preferably of about 250 ms. The search interval may be set to start 250 ms before the time point of mitral valve closure and to end at the time point of mitral valve closure. In other embodiments, the search window starts at the P-wave and has a duration of 200-280 ms, and preferably of 220-260 ms, and more preferably of about 250 ms. In embodiments of the present invention, the search window has a length of the AV delay of the cardiac stimulator and starts at the P-wave. The maximum positive rate of change of the A-wave of the LAP signal or the maximum value of the derivative of the LAP signal within the search window is defined as the most positive slope of the LAP signal.

The microcontroller 41 further includes an optimizing module 48 coupled to the LAP signal processing module 65 and being configured to adjust or optimize an AV and/or VV delay in response to the minimum of the maximum positive rate of change of the A-wave.

The aforementioned component or components of the microcontroller 41 may be implemented as part of the microcontroller 41, or as software/firmware instructions programmed into the device and executed on the microcontroller 41 during certain modes of operation.

Figure 3E:
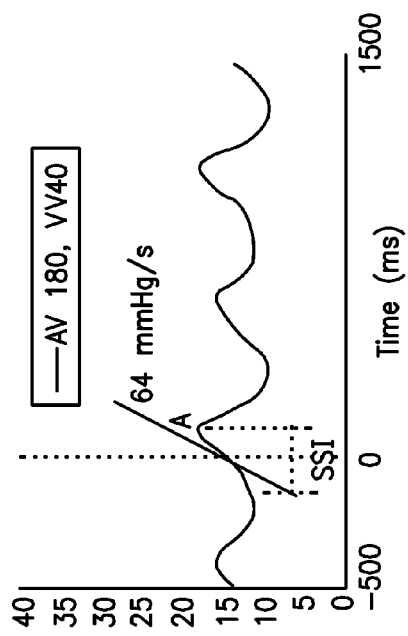
Figure 3F:
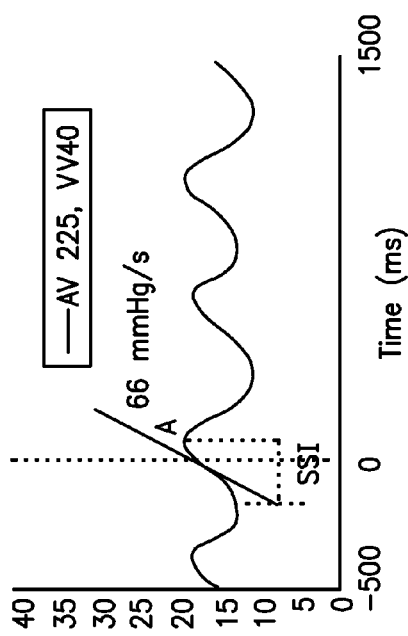
Figure 3G:
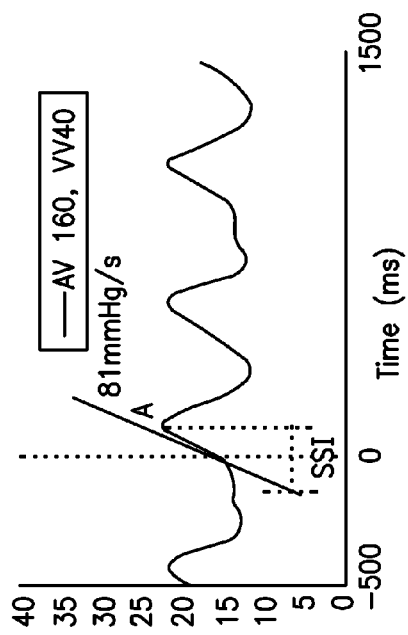
Figure 3H:
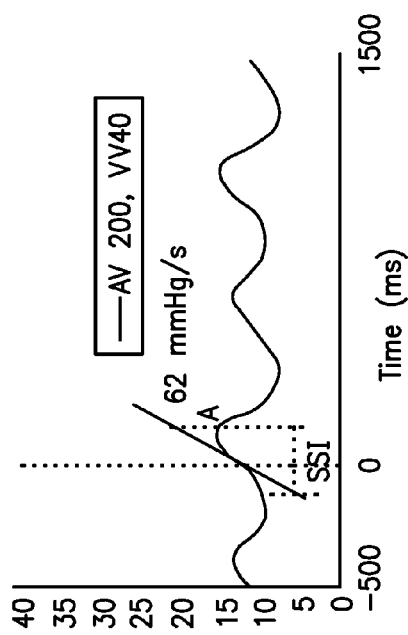
Figure 5:
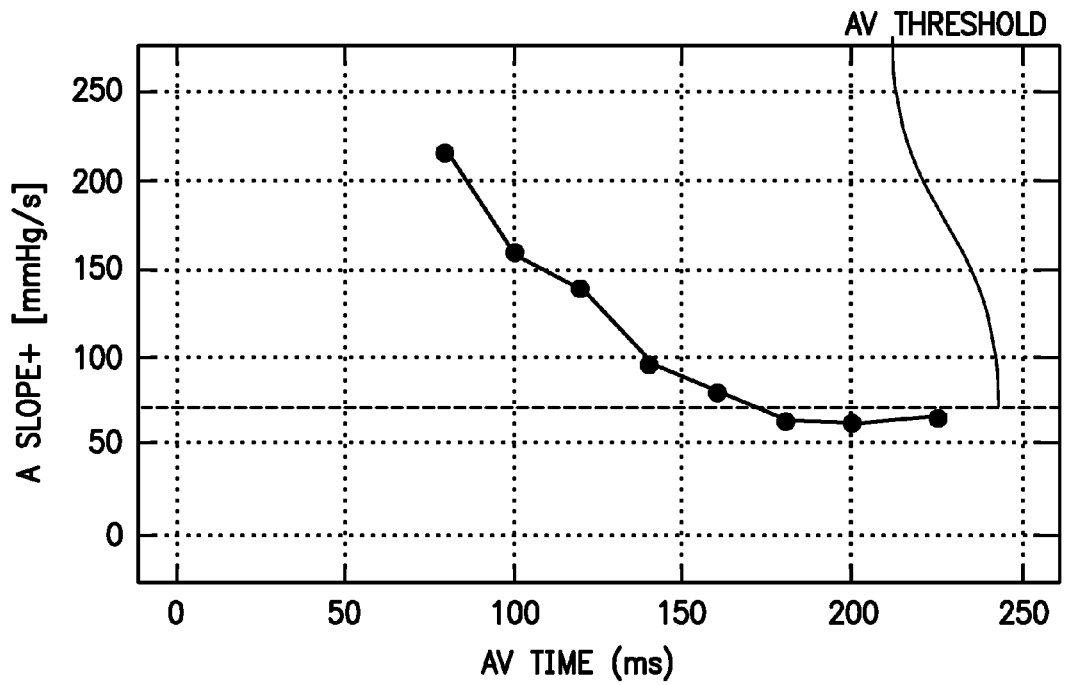
FIG. 5 shows the maximum positive rate of change of the A-wave as a function of AV delay.
Figure 6:
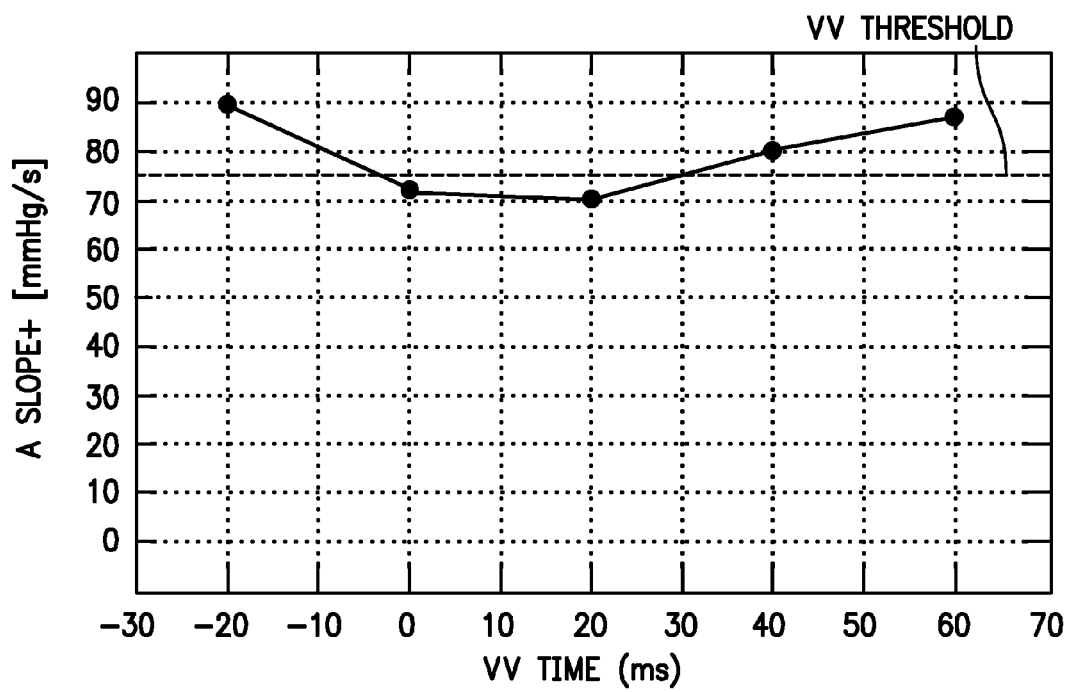
FIG. 6 shows the maximum positive rate of change of the A-wave as a function of VV delay.

A reduction of the maximum positive rate of change of the A-wave indicates an enhanced hemodynamic performance. For example, the adjustment or optimizing can be performed as a grid search to find the optimal combination of AV and VV delay. In the grid search, a matrix of AV and VV delays may be selected and the maximum positive rate of change of the A-wave for combinations of AV and VV delays in the matrix is determined. The combination of AV and VV delays corresponding to a minimum of the maximum positive rate of change of the A-wave or corresponding to a value of the maximum positive rate of change of the A-wave below a predetermined threshold (see FIGS. 5 and 6) is determined to be an optimal AV and VV delay. Alternatively, an optimal AV delay can be determined in a first step by varying the AV delay to minimize the maximum positive rate of change of the A-wave having a fixed VV delay. When the optimal AV delay has been determined, the optimal VV delay is identified by varying the VV delay to minimize the maximum positive rate of change of the A-wave at a fixed AV delay (preferably the previously determined optimal AV delay). With reference to FIGS. 3a-3h, 4a-4d, 5 and 6, test results from an optimizing performed on a patient are shown. In FIG. 3a-3h, the maximum positive rate of change of the A-wave for a number of different AV delays (a range of 80 ms-225 ms) and at a constant VV delay of 40 ms are shown (where LV is stimulated first). As can be seen in FIG. 3g, the minimum value (62 mmHg/s) of the maximum positive rate of change of the A-wave is obtained at an AV delay of 200 ms. SSI indicates the slope search interval. With reference to FIG. 4a-4d, the AV delay of 200 ms providing the minimum value (62 mmHg/s) of the maximum positive rate of change of the A-wave is used when optimizing the VV delay. As illustrated in FIG. 4b, the VV delay of 20 ms provides the minimum value (70 mmHg/s) of the maximum positive rate of change of the A-wave. Based on these results, an optimal combination of AV and VV delay can be determined to be an AV delay of 200 ms and a VV delay of 40 ms. In FIG. 5, the value (in mmHg/s) of the maximum positive rate of change of the A-wave (A slope+) is plotted against different AV delays using a fixed VV delay of 40 ms, and, in FIG. 6, the value (in mmHg/s) of the maximum positive rate of change of the A-wave is plotted against different VV delays (where LV is stimulated first if the delay is positive and RV is stimulated first if the delay is negative) using a fixed AV delay of 200 ms (i.e. the AV delay providing the minimum value (70 mmHg/s) of the maximum positive rate of change of the A-wave). In FIG. 5, an arbitrary and exemplary AV threshold for use in optimizing the AV interval is also shown. The exemplary AV threshold is set to 75 mmHg/s. If this AV threshold had used for optimizing the AV delay, the AV delay of 180 ms (see FIG. 3f) may have been determined to be the optimal delay instead of an AV delay of 200 ms. Further, with reference to FIG. 6, an arbitrary and exemplary VV threshold is also shown. The exemplary VV threshold is set to 75 mmHg/s. If this VV threshold had used for optimizing the AV delay, the AV delay of 180 ms (see FIG. 3f) may have been determined to be the optimal delay instead of an AV delay of 200 ms.

As discussed above, the threshold is patient specific and drug specific and will hence have to be determined for each individual patient and the threshold may have to be adjusted if, for example, a new drug regime is implemented for the patient. The threshold may be determined on empirical data for the specific patient, for example, based on results from earlier optimizations of the AV and VV delay.

With reference now to FIG. 7, an embodiment of the method for adjusting the AV and VV delay of a cardiac stimulator according to the present invention will be discussed. FIG. 7 is a flow diagram of an AV and VV delay adjustment process S100, which may be performed by a cardiac stimulator configured in accordance with an example embodiment of the inventions, for example, as illustrated in FIG. 2. The various tasks performed in connection with the process S100 may be performed by software, hardware, firmware, or any combination thereof. For illustrative purposes, the following description of the process S100 refers to elements mentioned above in connections with FIGS. 1-6. In practical embodiments, portions of the process S100 may be performed by different elements of the described cardiac stimulator. It should be appreciated that the process S100 may include any number of additional or alternative tasks, the tasks shown in FIG. 7 need not be performed in the illustrated order, and the process S100 may be incorporated into a more comprehensive procedure or process having additional functionality not described in detail herein.

The process S100 obtains a LAP signal, task S110, using the data collection module 62 which is configured to obtain data about the patient including LAP signals from the LAP sensor 72. The process S100 may use different protocols for varying or adjusting the AV and VV delays. For example, a fixed VV delay determined by means of an optimization algorithm such as QuickOpt™, provided by the applicant, and a set of different AV delays can be evaluated to find the optimal AV delays in a first step. Thereafter, the optimal AV delay is used as fixed AV delay and a set of VV delays are evaluated to find the optimal VV delay. Such a process is described below. Another option is to perform a full-grid search, which means that all combinations of a matrix of AV and VV delays are evaluated to find the optimal combination of an AV delay and a VV delay.

The LAP signals from the LAP sensor 72 may be amplified and converted from raw analog data into digital signals. The LAP signal is obtained at a first pacing interval setting including an AV delay and a VV delay, for example, with reference to FIG. 3a, an AV delay of 80 ms and a VV delay of 40 ms.

In task S120, the digital LAP signals are pre-processed. For example, the LAP signal processing module 65 may perform a band-pass filtering procedure using a band-pass range of 0.75 Hz-30 Hz to remove high frequency noise and respiration artifacts. At task S130, the A-wave is identified in the LAP signal or in the derivative of the LAP signal.

At task S140, a maximum positive rate of change of the A-wave of the

LAP signal is determined within a predetermined search window as discussed above. Thus, a maximum positive rate of change of the A-wave of the LAP signal for the AV delay of 80 ms and the VV delay of 40 ms is determined, which, with reference to FIG. 3a, is 215 mmHg/s.

In query task S150, it is checked whether all combinations of AV delays and fixed VV delay have been evaluated with respect to the maximum positive rate of change of the A-wave of the LAP signal. With reference to FIGS. 3a-3h, the AV delays to be evaluated are: 80 ms, 100 ms, 120 ms, 140 ms, 160 ms, 180 ms, 200 ms, 225 ms. The VV delay is fixed to 40 ms, which may have been determined by use of, for example, QuickOpt™. If not all AV delays have been evaluated, the AV delay is adjusted in task S160 and the above tasks S110-S140 are repeated for the new or adjusted combination of AV and VV delay. If all AV delays in the protocol have been evaluated, the minimum value of the maximum positive rate of change of the A-wave of the LAP signal is selected in task S170 as the optimal AV delay and is stored for use in the further optimization process.

With reference to FIGS. 3a-3h, the minimum value of the maximum positive rate of change of the A-wave of the LAP signal is 62 mmHg/s (AV delay 200 ms and VV delay 40 ms).

The query task S150 may include a comparison between the present value of the maximum positive rate of change of the A-wave of the LAP signal (i.e. for the present combination of AV and VV delay) and the preceding value of the maximum positive rate of change of the A-wave of the LAP signal (i.e. for the preceding combination of AV and VV delay). If the present value is lower the preceding value, the process S100 is continued. On the other hand, if the preceding value is lower than the present value, the preceding value indicates a more optimal cardiac function and the process S100 proceeds with the corresponding tasks S180-S210 but with a varying VV delay and a fixed AV delay (preferably the optimal AV delay found in task S150). By performing this comparison after each evaluation of a combination of AV and VV delay, it may be possible to obtain an optimal value of the maximum positive rate of change of the A-wave of the LAP signal faster compared to a process where all AV delays are evaluated. In the illustrated case, all AV delays would however have to be evaluated because the last but one combination of delays provided the lowest value of the maximum positive rate of change of the A-wave of the LAP signal (see FIGS. 3g and 3h).

In query task S210, it is checked whether all combinations of VV delay and fixed AV delay have been evaluated with respect to the maximum positive rate of change of the A-wave of the LAP signal. With reference to FIGS. 4a-4d, the VV delays to be evaluated are: 0 ms, 20 ms, 40 ms, and 60 ms. The AV delay is fixed to 200 ms, i.e. the optimal AV delay determined in the previous steps. If not all VV delays have been evaluated, the above tasks S180-S210 are repeated for the new or adjusted combination of AV and VV delay. If all VV delays have been evaluated, the minimum value of the maximum positive rate of change of the A-wave of the LAP signal is selected in task S220 as the optimal VV delay and is stored for possible use when stimulating the patient together with the optimal AV delay.

With reference to FIGS. 4a-4d, the minimum value of the maximum positive rate of change of the A-wave of the LAP signal is 70 mmHg/s (AV delay 200 ms and VV delay 20 ms).

The query task S210 may include a comparison between the present value of the maximum positive rate of change of the A-wave of the LAP signal (i.e. for the present combination of AV and VV delay) and the preceding value of the maximum positive rate of change of the A-wave of the LAP signal (i.e. for the preceding combination of AV and VV delay). If the present value is lower the preceding value, the process S100 is continued. On the other hand, if the preceding value is lower than the present value, the preceding value indicates a more optimal cardiac function and the process S100 proceeds with the corresponding tasks S180-S210 but with a varying VV delay and a fixed AV delay (preferably the optimal AV delay found in task S150). By performing this comparison after each evaluation of an AV and a VV delay, it may be possible to obtain an optimal value of the maximum positive rate of change of the A-wave of the LAP signal faster compared to a process where all AV delays are alternately evaluated. In the illustrated case, the VV delay optimizing process would have been terminated after the evaluation of the combination of an AV delay of 200 ms and a VV delay of 40 ms because the present value of the maximum positive rate of change of the A-wave of the LAP signal was 80 mmHg/s and the preceding value was 70 mmHg/s, i.e. lower than the present value. When a combination of optimal AV and VV delays has been found, the process S100 can be terminated.

Although modifications and changes may be suggested by those skilled in the art, it is the intention of the inventors to embody within the patent warranted hereon all changes and modifications as reasonably and properly come within the scope of their contribution to the art.

What is claimed is:

1. A cardiac stimulator comprising:
   a data collection module configured to obtain at least one left atrial pressure (LAP) signal representing cardiac behavior over a cardiac cycle of a heart, from a left atrial pressure sensor;
   a stimulation pulse generator module configured to generate and emit stimulation pulses with a timing between successive pulses that implements at least one of an AV delay and VV delay;
   an LAP signal processing module in communication with said data collection module, said LAP signal processing module being configured to identify an A-wave of the heart using the LAP signal, and to determine a maximum positive rate of change of the A-wave; and
   a parameter setting adjusting module in communication with said LAP signal processing module, said parameter setting adjusting module being configured to adjust said at least one of said AV delay and said VV delay to produce a reduction of said maximum positive rate of change of the A-wave.

2. A cardiac stimulator as claimed in claim 1 wherein said parameter setting adjusting module is configured to optimize said at least one of said AV delay and said VV delay by setting said at least one of said AV delay and said VV delay to a delay value that minimizes said maximum positive rate of change of the A-wave.

3. A cardiac stimulator as claimed in claim 1 wherein said parameter setting adjusting module is configured to optimize said at least one of said AV delay and said VV delay by setting said at least one of said AV delay and said VV delay to a delay value that causes said maximum positive rate of change of the A-wave to be below a predetermined threshold.

4. A cardiac stimulator as claimed in claim 1 wherein said LAP signal processing module is configured to calculate a time derivative of LAP signal in said cardiac cycle, and to determine said maximum positive rate of change of the A-wave by identifying a maximum value of said time derivative of the LAP signal within a search window having a predetermined time duration.

5. A cardiac stimulator as claimed in claim 4 comprising a P-wave detector that detects a P-wave of the heart in said cardiac cycle, and wherein said parameter setting adjusting module is configured to start said time duration of said search window at said P-wave and to give said time duration a value selected from the group consisting of between 200 and 280 ms, between 220 and 260 ms, and approximately 250 ms.

6. A cardiac stimulator as claimed in claim 5 wherein said parameter setting adjusting module is configured to set said time duration of said search window to start at said P-wave and to have a duration equal to a duration of said AV delay.

7. A cardiac stimulator as claimed in claim 4 wherein said LAP signal processing module is configured to identify a point in time of mitral valve closure (MC) in the heart, from said LAP signal, and wherein said parameter setting adjustment module is configured to set said time duration of said search window to start at a start time between 200 and 280 ms before the point in time of MC, between 220 and 260 ms before the point in time of MC, and approximately 250 ms before the point in time of MC, and to end at the point in time of MC.

8. A cardiac stimulator as claimed in claim 1 wherein said LAP signal processing module is configured to determine said maximum rate of change of the A-wave by determining a maximum slope of said LAP signal within a search window having a predetermined time duration.

9. A cardiac stimulator as claimed in claim 8 comprising a P-wave detector that detects a P-wave of the heart in said cardiac cycle, and wherein said parameter setting adjusting module is configured to start said time duration of said search window at said P-wave and to give said time duration a value selected from the group consisting of between 200 and 280 ms, between 220 and 260 ms, and approximately 250 ms.

10. A cardiac stimulator as claimed in claim 8 wherein said LAP signal processing module is configured to identify a point in time of mitral valve closure (MC) in the heart, from said LAP signal, and wherein said parameter setting adjustment module is configured to set said time duration of said search window to start at a start time between 200 and 280 ms before the point in time of MC, between 220 and 260 ms before the point in time of MC, and approximately 250 ms before the point in time of MC, and to end at the point in time of MC.

11. A cardiac stimulator as claimed in claim 10 wherein said LAP signal processing module is configured to identify said point in time MC by identifying a peak of the A-wave.

12. A cardiac stimulator as claimed in claim 1 wherein said LAP signal processing module is configured to determine the maximum positive rate of change of the A-wave for combinations of AV and VV delays in a matrix of AV and VV delays, and wherein said parameter setting adjusting module is configured to determine a combination of AV and VV delays corresponding to a minimum of the maximum positive rate of change of the A-wave or corresponding to a value of the maximum positive rate of change of the A-wave below a predetermined threshold to be optimal AV and VV delays.

13. A cardiac stimulator as claimed in claim 1:
wherein said LAP signal processing module is configured to determine the maximum positive rate of change of the A-wave for combinations of AV delays and a fixed VV delay and to identify the AV delay providing the minimum of the maximum positive rate of change of the A-wave or corresponding to a value of the maximum positive rate of change of the A-wave below a predetermined threshold;
wherein said parameter setting adjusting module is configured to select a set of VV delays and said AV delay providing the minimum of the maximum positive rate of change of the A-wave or corresponding to a value of the maximum positive rate of change of the A-wave below a predetermined threshold;
wherein said LAP signal processing module is further configured to determine the maximum positive rate of change of the A-wave for combinations of VV delays and the fixed AV delay and to identify the VV delay providing the minimum of the maximum positive rate of change of the A-wave or corresponding to a value of the maximum positive rate of change of the A-wave below a predetermined threshold; and
wherein said parameter setting adjusting module is further configured to determine the AV delay and the VV delay corresponding to a minimum of the maximum positive rate of change of the A-wave or corresponding to a value of the maximum positive rate of change of the A-wave below a predetermined threshold to be optimal AV and VV delays.

\* \* \* \* \*